United States Patent
Tsai et al.

(10) Patent No.: US 9,733,067 B2
(45) Date of Patent: Aug. 15, 2017

(54) APPARATUS FOR DETECTING HEIGHTS OF DEFECTS ON OPTICAL GLASS

(71) Applicants: Hong-I Tsai, Taipei (TW); Chang-Chien Mu, Taipei (TW)

(72) Inventors: Hong-I Tsai, Taipei (TW); Chang-Chien Mu, Taipei (TW)

(73) Assignee: Taiwan Nano-Technology Application Corp, Hsinchu (TW)

( * ) Notice: Subject to any disclaimer, the term of this patent is extended or adjusted under 35 U.S.C. 154(b) by 160 days.

(21) Appl. No.: 14/938,852

(22) Filed: Nov. 12, 2015

(65) Prior Publication Data

US 2016/0061584 A1    Mar. 3, 2016

(51) Int. Cl.

| | |
|---|---|
| *G01B 11/06* | (2006.01) |
| *F16M 11/04* | (2006.01) |
| *F16M 11/18* | (2006.01) |
| *G01N 15/02* | (2006.01) |
| *G01N 15/00* | (2006.01) |

(52) U.S. Cl.
CPC ....... *G01B 11/0608* (2013.01); *F16M 11/048* (2013.01); *F16M 11/18* (2013.01); *G01N 15/0205* (2013.01); *G01N 2015/0061* (2013.01)

(58) Field of Classification Search
CPC .................................................. G01B 11/0608
See application file for complete search history.

(56) References Cited

U.S. PATENT DOCUMENTS

| | | | | | |
|---|---|---|---|---|---|
| 2,920,525 | A | * | 1/1960 | Appel ................. | G01N 21/255 250/564 |
| 5,087,121 | A | * | 2/1992 | Kakuchi ............... | G01B 11/22 356/626 |
| 5,134,665 | A | * | 7/1992 | Jyoko ................. | G01B 11/0608 348/87 |
| 8,351,709 | B2 | * | 1/2013 | Hayashi ............ | G01B 11/0608 382/203 |
| 2007/0114397 | A1 | * | 5/2007 | Hayakawa ......... | G01N 23/2251 250/307 |
| 2014/0009601 | A1 | * | 1/2014 | Cho .................... | G01B 11/0608 348/126 |

* cited by examiner

*Primary Examiner* — Charlie Y Peng

(57) ABSTRACT

A detection apparatus includes four sets of transmitter and receiver wherein the transmitters are on a first sliding member of a frame and the receivers are on a second sliding member of the frame; and drives for moving the first and second sliding members back and forth. During the movements of the first and second sliding members, each transmitter emits laser beam toward the receiver of the same set by passing through a space above a photoresist-coated optical glass by 100 μm, no signal is generated at the receiver if the laser beam is not blocked, and a signal is generated at the receiver if the laser beam is blocked by at least one of a plurality of particles on the photoresist-coated optical glass.

1 Claim, 6 Drawing Sheets

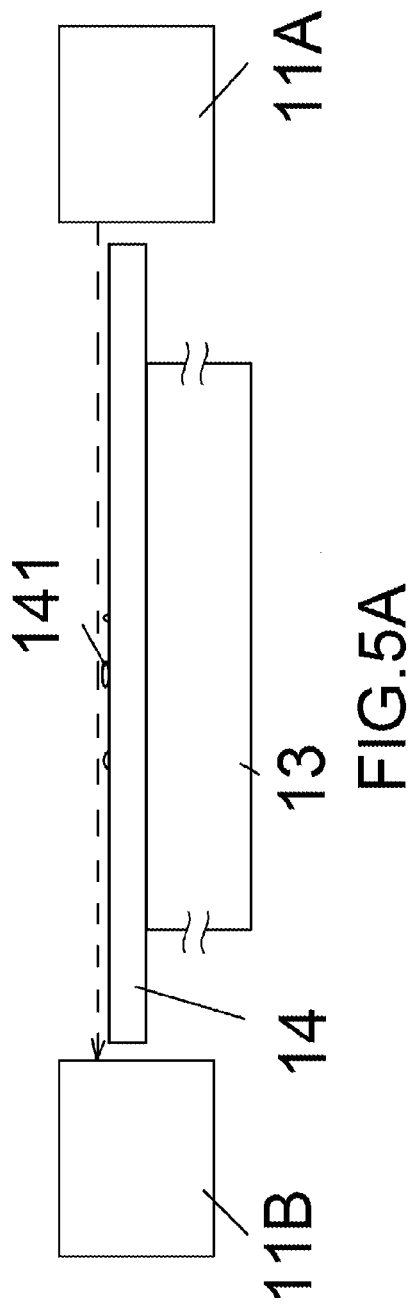
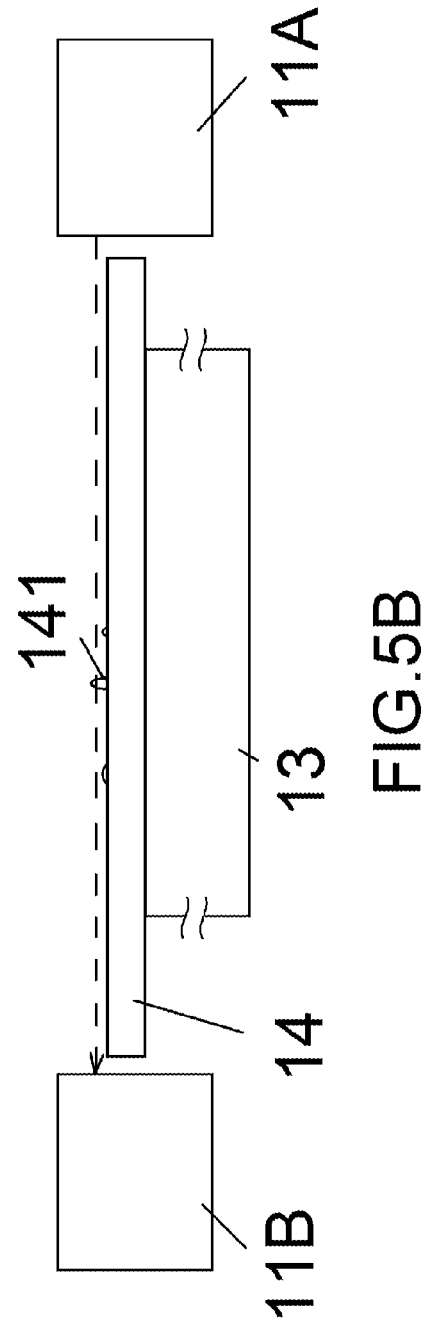

| particle size: Width ≧ 1mm | Particle (height) | Success rate | | | |
|---|---|---|---|---|---|
| | 150μm | ≧ 95% | | | |
| | 120μm | ≧ 90% | | | |
| | 100μm | ≧ 85% | | | |
| glass thickness (mm) | 0.33 | 0.4 | 0.5 | 1.1 | 1.1-1.8 |

FIG.6

| count | Particle height | deviation | Δ voltage | Δ Shifting voltage |
|---|---|---|---|---|
| 1 | 0.303 mm | 10.0025 mm | 0.302 | 0.017 |
| 2 | 0.343 mm | 10.0025 mm | 0.322 | 0.125 |
| 3 | 0.352 mm | 10.0025 mm | 0.352 | 0.510 |
| 4 | 0.376 mm | 10.0025 mm | 0.312 | 0.130 |

FIG.7

APPARATUS FOR DETECTING HEIGHTS OF DEFECTS ON ON OPTICAL GLASS

BACKGROUND OF THE INVENTION

1. Field of the Invention

The invention relates to semiconductor device fabrication and more particularly to an apparatus for detecting heights of particles on a photoresist-coated optical glass in the steps of photolithography.

2. Description of Related Art

As shown in FIG. 1, conventional photolithography includes several steps in sequence. For example, after drying and cooling a photoresist-coated optical glass (glass in short), exposure and developing steps are performed on the glass. It is known that top of the glass may have defects (e.g., particles). It is also known that heights of particles on the glass are required to be less than a set value, for example, 100 μm. Otherwise, an expensive mask subsequently placed on the glass may be damaged by the particles and this is undesired. Thus, an apparatus for detecting heights of particles on a glass in the steps of photolithography is required.

A conventional apparatus for detecting heights of particles on a glass in the steps of photolithography is shown in FIG. 2. The apparatus is a gantry type and comprises a transmitter A, a receiver B, and a bridge C having two ends secured to the transmitter A and receiver B respectively. A rectangular glass D is placed on a stage E which is mounted between the transmitter A and receiver B. The transmitter A and the receiver move toward the same direction in synchronous in a defect detection operation. The transmitter A can emit laser beam (indicated by dotted lines) toward the receiver B and the laser beam transversely passes through a space about 150-200 μm above the glass D. No signal is generated at the receiver B if there is no particle having a height less than 150 μm. To the contrary, a signal is generated at the receiver 1B if the laser beam is blocked by a particle F having a height equal to or more than 150 μm. The signal is converted into a representation of unacceptable defect after a processing.

The synchronous movement of the transmitter A and receiver B is the advantage of the conventional apparatus. However, the conventional apparatus also has a disadvantage of having a fixed distance between the transmitter A and receiver B. That is, an adjustment of the distance between the transmitter A and receiver B is impossible. This greatly decreases the application of the conventional apparatus because widths of the glasses F produced by different companies are not the same. In short, the conventional apparatus is applicable to a limited number of applications. Further, particles having a height in the range of 100-150 μm cannot be detected. Unfortunately, the particles can still damage a mask if the mask is placed on the glass in a subsequent manufacturing step. Furthermore, a tact time is about 30 seconds and is unacceptable. Thus, the need for improvement still exists.

SUMMARY OF THE INVENTION

It is therefore one object of the invention to provide a detection apparatus, comprising a frame including first and second supports on tops of two sides respectively, first and second sliding members on the first and second supports respectively, two front interconnecting members having two ends releasably secured to front ends of the supports respectively, and two rear interconnecting members having two ends releasably secured to rear ends of the supports respectively; a plurality of sets of transmitter and receiver wherein the transmitters are equally spaced on the first sliding member, the receivers are equally spaced on the second sliding member, the transmitter and the receiver of each set are at the same elevation, and a distance between the transmitter and the receiver of each set is between 1,100 mm and 2,500 mm; first drive means for moving the first sliding member back and forth; and second drive means for moving the second sliding member back and forth; wherein the first and second sliding members are configured to synchronously move toward either a rear end of the frame in a first direction or a front end of the frame in a second direction; wherein at least one of the transmitter and the receiver is configured to deviate from a straight line interconnecting the transmitter and the receiver by no more than 10 μm; wherein during the movements of the first and second sliding members, each transmitter emits laser beam toward the receiver of the same set by passing through a space above a photoresist-coated optical glass by 100 μm, no signal is generated at the receiver if the laser beam is not blocked, and a signal is generated at the receiver if the laser beam is blocked by at least one of a plurality of particles on the photoresist-coated optical glass; and wherein the movement of the first and second sliding members in the first direction is reversed to the second direction after reaching a predetermined position at the rear end of the frame.

The above and other objects, features and advantages of the invention will become apparent from the following detailed description taken with the accompanying drawings.

BRIEF DESCRIPTION OF THE DRAWINGS

FIG. 5A is a block diagram showing no defect detected on the photoresist-coated optical glass when laser beam emitted by the particle passes through space above photoresist-coated optical glass prior to being received by the transmitter;

FIG. 5B is a view similar to FIG. 5A showing defect on the photoresist-coated optical glass being detected;

FIG. 6 is a table showing success rates of the detection apparatus of the invention; and FIG. 7 is an enlarged photograph showing defect information on the display screen.

DETAILED DESCRIPTION OF THE INVENTION

Figure 1:
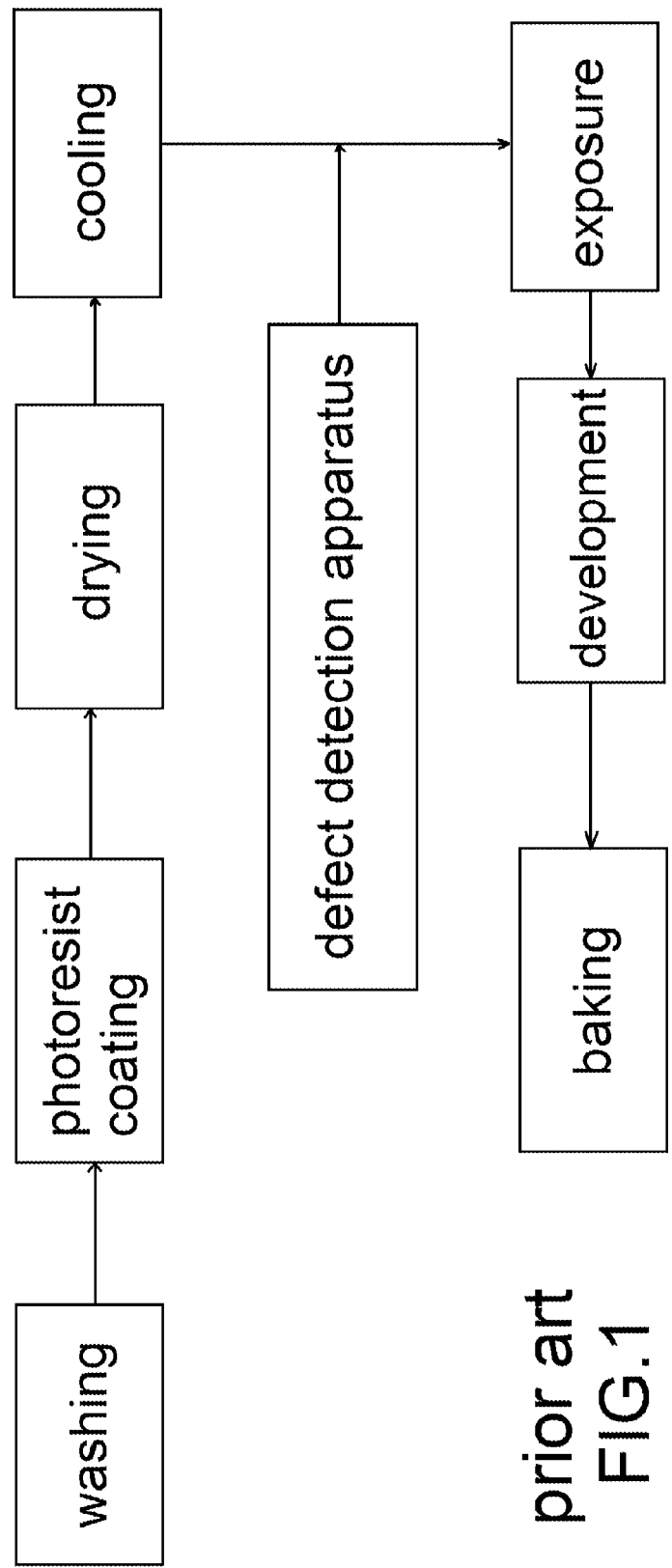
FIG. 1 is a block diagram of steps of conventional photolithography.
Figure 2:
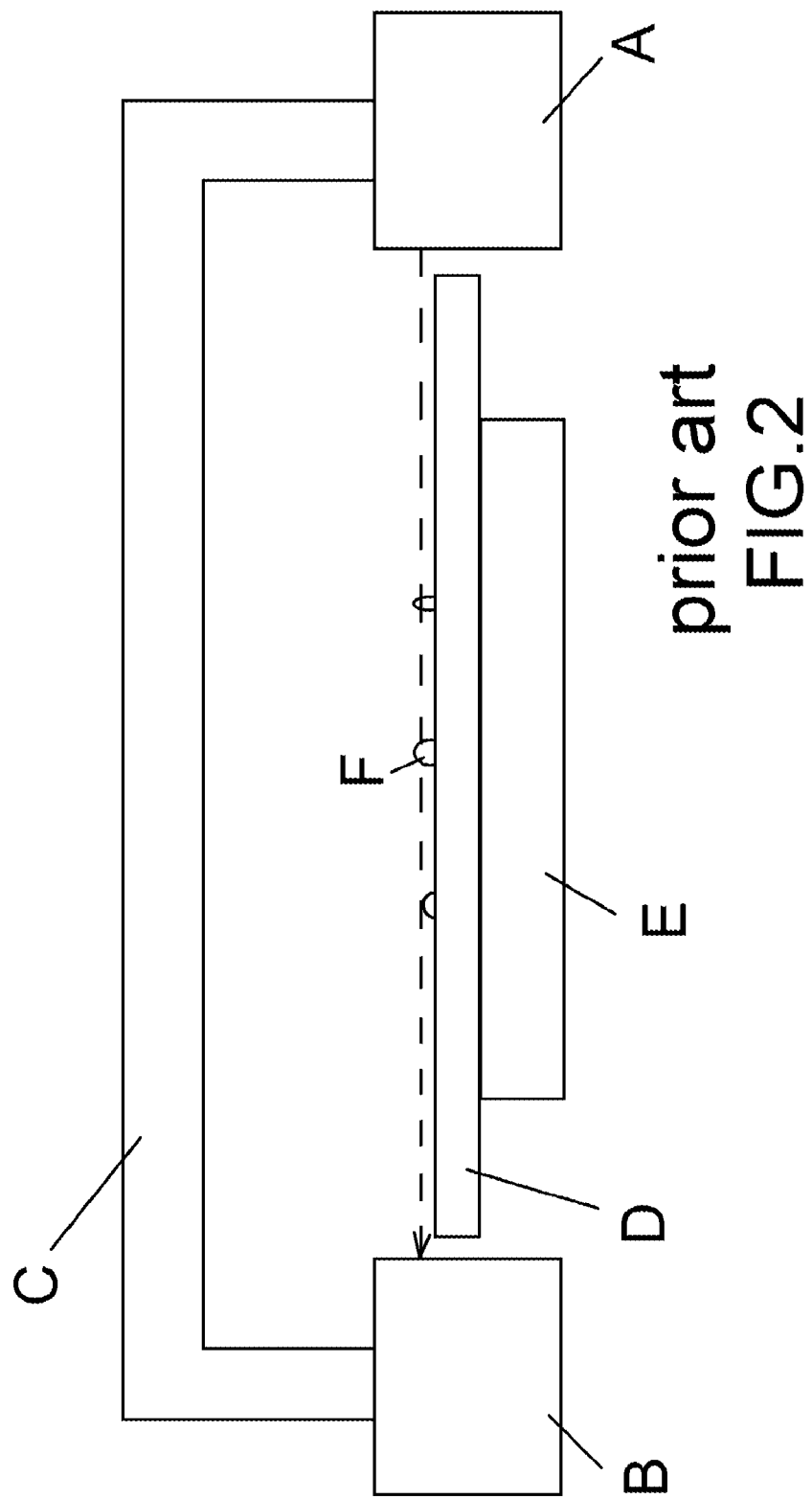
FIG. 2 is a schematic front view of a conventional gantry type apparatus for detecting heights of particles on a glass in the steps of photolithography.
Figure 3:
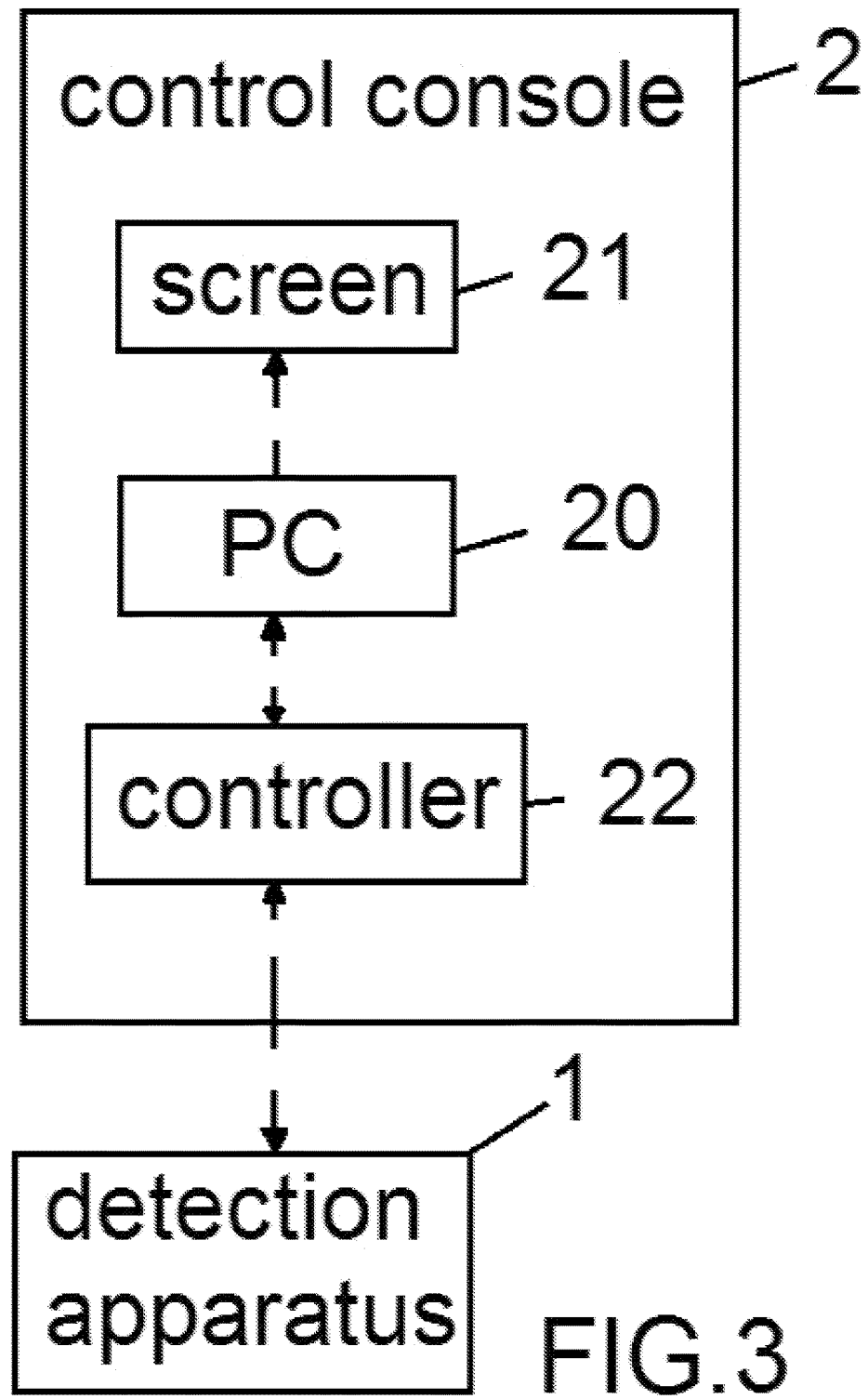
FIG. 3 is a block diagram of a detection system according to the invention.
Figure 4:
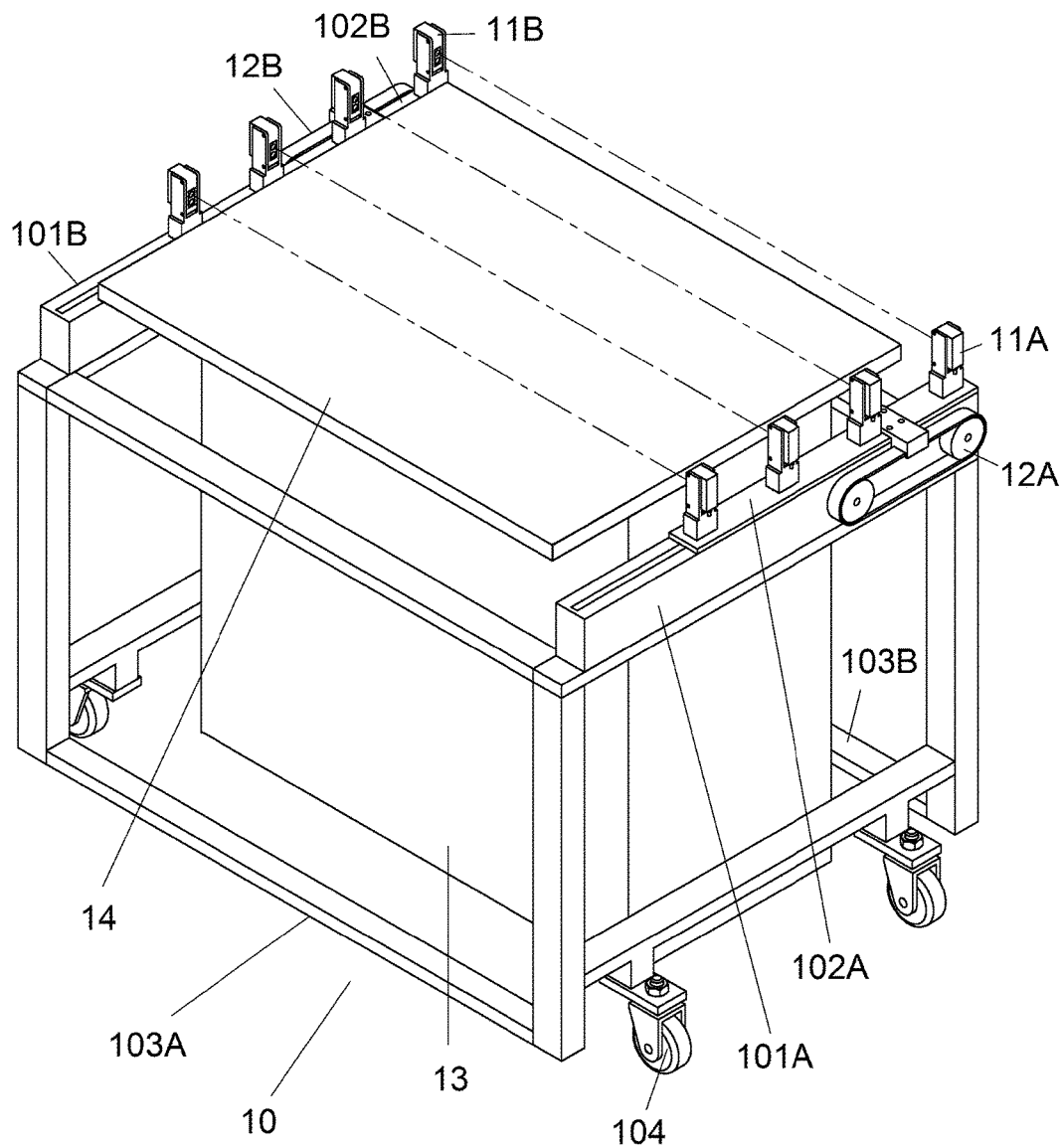
FIG. 4 is a perspective view of the detection apparatus with a stage disposed therein and a photoresist-coated optical glass placed on the stage.

Referring to FIGS. 3 to 7, a detection system in accordance with the invention comprises a detection apparatus 1 and a control console 2 as discussed in detail below.

The control console 2 includes a personal computer (PC) 20 having a display screen 21, and a controller 22 electronically connected to the PC 20. Signals can be sent from the controller 22 to the PC 20 or vice versa.

The detection apparatus 1, as the subject of the invention, includes a frame 10 having two parallel supports 101A, 101B on tops of two sides respectively, two sliding members 102A, 102B on the supports 101A, 101B respectively, two front interconnecting members 103A each having two ends releasably secured to front ends of the supports 101A, 101B respectively, two rear interconnecting members 103B having two ends releasably secured to rear ends of the supports 101A, 101B respectively, and four wheels (only three are shown) 104 rotatably mounted on bottoms of the supports 101A, 101B; four sets of transmitter 11A and receiver 11B in which the transmitters 11A are equally spaced on the sliding member 102A, and the receivers 11B are equally spaced on the sliding member 102B; and two chain drives 12A, 12B for moving the sliding members 102A and 102B back and forth respectively.

Preferably, the transmitters 11A and the receivers 11B are charged-coupled devices (CCD), i.e., electronic light sensors. Specifically, the transmitters 11A and the receivers 11B are laser diode based sensors. Further, a distance between the transmitter 11A and the receiver 11B of each set is between 1,100 mm and 2,500 mm, i.e., the detection apparatus 1 being adjustable for accommodating different widths of glasses produced by different companies.

It is noted that the supports 101A, 101B are adapted to absorb a great portion of vibration and jarring in a defect detection operation, thereby greatly increasing success rates of detecting defects as discussed below.

In a defect detecting operation of the invention, a stage 13 is disposed in the detection apparatus 1. A rectangular photoresist-coated optical glass (i.e., glass in short) 14 is placed on the stage 13. The transmitter 11A and the receiver 11B of each set and the glass 14 are at the same elevation. After the chain drives 12A and 12B activated by the controller 22, the sliding members 102A and 102B synchronously move toward the rear end of the glass 14. It is noted that vibration is a mechanical phenomenon and it should be minimized. Thus, at least one of the transmitter 11A and the receiver 11B is allowed and configured to deviate from a straight line interconnecting the transmitter 11A and the receiver 11B by no more than 10 µm. This is because the deviation more than 10 µm may decrease accuracy of the detection.

The transmitter 11A emits laser beam toward the receiver 11B of the same set and the laser beam transversely passes through a space above the glass 14 by 100 µm. No signal is generated at the receiver 11B if there is no defect on the glass 14 (see FIG. 5A). To the contrary, a signal is generated at the receiver 11B if the laser beam is blocked by at least one of a plurality of particles 141 having a height of at least 100 µm on the glass 14. That is, the invention can detect defects having a height as low as 100 µm. This is a great improvement in comparison with the conventional defect detection apparatus which can only detect defects having a height as low as 150 µm. The signal is sent to the controller 22 to be processed by Common Information Model (CIM).

Each transmitter 11A (or receiver 11B) travels a distance of 25% of the length of the glass 14 (i.e., the length of the glass 14 divided by four representing four sets of transmitter 11A and receiver 11B). The movement of the sets of transmitter 11A and receiver 11B will be stopped after the whole length of the glass 14 has been scanned by the laser beams. Immediately next, each of the chain drives 12A and 12B reverses its moving direction to bring the sets of transmitter 11A and receiver 11B back to its starting position. This completes a scanning cycle.

Preferably, the laser beam has a wavelength of 660 nm and a pulse width of 48 µm.

Preferably, tact time, i.e., scanning cycle, of the invention is 5 second which is a great improvement of the prior art which has a tact time of 30 second.

Preferably, dimensions of the glass 14 are 1300 mm (W)×1300 mm (L).

Referring to FIG. 6, very high success rates of the detection apparatus of the invention are shown.

Referring to FIG. 7, it shows defect information.

While the invention has been described in terms of preferred embodiments, those skilled in the art will recognize that the invention can be practiced with modifications within the spirit and scope of the appended claims.

What is claimed is:

1. A detection apparatus, comprising:
   a frame including first and second supports on tops of two sides respectively, first and second sliding members on the first and second supports respectively, two front interconnecting members having two ends releasably secured to front ends of the supports respectively, and two rear interconnecting members having two ends releasably secured to rear ends of the supports respectively;
   a plurality of sets of transmitters and receivers wherein the transmitters are equally spaced on the first sliding member, the receivers are equally spaced on the second sliding member, the transmitter and receiver of each set of the plurality of sets of transmitters and receivers are at the same elevation, and a distance between the transmitter and the receiver of each set is between 1,100 mm and 2,500 mm;
   first drive means for moving the first sliding member back and forth; and
   second drive means for moving the second sliding member back and forth;
   wherein the first and second sliding members are configured to synchronously move toward either a rear end of the frame in a first direction or a front end of the frame in a second direction;
   wherein at least one of the transmitter and the receiver is configured to deviate from a straight line interconnecting the transmitter and the receiver by no more than 10 µm;
   wherein during the movements of the first and second sliding members, each transmitter emits laser beam toward the receiver of the same set by passing through a space above a photoresist-coated optical glass by 100 µm, no signal is generated at the receiver if the laser beam is not blocked, and a signal is generated at the receiver if the laser beam is blocked by at least one of a plurality of particles on the photoresist-coated optical glass; and
   wherein the movement of the first and second sliding members in the first direction is reversed to the second direction after reaching a predetermined position at the rear end of the frame.

* * * * *